United States Patent [19]

Hammond et al.

[11] Patent Number: 5,374,718
[45] Date of Patent: Dec. 20, 1994

[54] NUCLEIC ACID PROBES TO CHLAMYDIA PNEUMONIAE

[75] Inventors: Philip Hammond; Anthony Endozo, both of San Diego, Calif.

[73] Assignee: Gen-Probe Incorporated, San Diego, Calif.

[21] Appl. No.: 936,533

[22] Filed: Aug. 26, 1992

[51] Int. Cl.$^5$ .................... C07H 21/00; C12Q 1/68
[52] U.S. Cl. ................... 536/24.32; 536/24.33; 435/6; 435/91.2; 935/77; 935/78
[58] Field of Search ............... 435/6, 91, 91.2; 536/27, 24.32, 24.33; 935/77, 78; 514/44

[56] References Cited

U.S. PATENT DOCUMENTS

| | | | |
|---|---|---|---|
| 4,851,330 | 7/1989 | Kohne | 435/6 |
| 5,030,557 | 7/1991 | Hogan et al. | 435/6 |

FOREIGN PATENT DOCUMENTS 8803957  6/1988  WIPO .

OTHER PUBLICATIONS

Holland et al J. Infect Dis (1990) 162: 984–987.
Campbell et al J. Clin Microbiol (Feb. 1992) 30: 434–439.
Gaydos et al J. Clin Microbiol (Apr. 1992) 30: 796–800.
Barry et al Bio/Technology (1990) 8: 233–236.
Campbell et al., 25 *J. Clin. Microbiol.* 1911, 1987, "Characterization of the New Chlamydia Agent, TWAR, as a Unique Organism by Restriction Endonuclease Analysis and DNA-DNA Hybridization".

*Primary Examiner*—Margaret Parr
*Assistant Examiner*—Carla Myers
*Attorney, Agent, or Firm*—Lyon & Lyon

[57] ABSTRACT

Hybridization assay probes specific for *Chlamydia pneumoniae* and no other Chlamydia species.

20 Claims, No Drawings

NUCLEIC ACID PROBES TO CHLAMYDIA PNEUMONIAE

FIELD OF THE INVENTION

The inventions described and claimed herein relate to the design and construction of nucleic acid probes to *Chlamydia pneumoniae* which are capable of detecting the organism in test samples of, e.g., sputum, urine, blood and tissue sections, food, soil and water.

BACKGROUND OF THE INVENTION

Two single strands of deoxyribo- ("DNA") or ribo- ("RNA") nucleic acid, formed from nucleotides (including the bases adenine (A), cytosine (C), thymidine (T), guanine (G), uracil (U), or inosine (I)), may associate ("hybridize") to form a double stranded structure in which the two strands are held together by hydrogen bonds between pairs of complementary bases. Generally, A is hydrogen bonded to T or U, while G is hydrogen bonded to C. At any point along the chain, therefore, one may find the classical base pairs AT or AU, TA or UA, GC, or CG. One may also find AG, GU and other "wobble" or mismatched base pairs.

When a first single strand of nucleic acid contains sufficient contiguous complementary bases to a second, and those two strands are brought together under conditions which will promote their hybridization, double stranded nucleic acid will result. Under appropriate conditions, DNA/DNA, RNA/DNA, or RNA/RNA hybrids may be formed.

A probe is generally a single stranded nucleic acid sequence which is complementary to some degree to a nucleic acid sequence sought to be detected ("target sequence"). It may be labelled with a detectable moiety such as a radioisotope, antigen or chemiluminescent moiety. A background description of the use of nucleic acid hybridization as a procedure for the detection of particular nucleic acid sequences is described by Kohne, U.S. Pat. No. 4,851,330, and Hogan et al., EPO Patent Application No. PCT/US87/03009, entitled "Nucleic Acid Probes for Detection and/or Quantitation of Non-Viral Organisms."

Hogan et al., supra, also describes methods for determining the presence of RNA-containing organisms in a sample which might contain such organisms. These methods require probes sufficiently complementary to hybridize to the ribosomal RNA (rRNA) of one or more non-viral organisms or groups of non-viral organisms. The mixture is then incubated under specified hybridization conditions, and assayed for hybridization of the probe and any test sample rRNA.

Hogan et al. also describes probes which detect only specifically targeted rRNA subunit subsequences in particular organisms or groups of organisms in a sample, even in the presence of many non-related organisms, or in the presence of the closest known phylogenetic neighbors. Specific examples of hybridization assay probes are provided for *Mycobacterium avium*, *Mycobacterium intracellulare*, *Mycobacterium tuberculosis*, *Mycobacterium africanum*, *Mycobacterium bovis*, *Mycobacterium microti*, the genus *Mycobacterium*, *Mycoplasma pneumoniae*, the genus *Legionella*, *Chlamydia trachomatis*, the genus *Campylobacter*, *Enterococcus*, the genus *Pseuomonas* group I, *Enterobacter cloacae*, *Proteus mirabilis*, the genus *Salmonella*, *Escherichia coli*, bacteria, fungi, and *Neisseria gonorrhoeae*. Such probe sequences do not cross react with nucleic acids from the groups listed above, or any other bacterial species or infectious agent, under appropriate hybridization stringency conditions.

SUMMARY OF THE INVENTION

This invention discloses and claims novel probes for the detection of *Chlamydia pneumoniae*. These probes are capable of distinguishing between *Chlamydia pneumoniae* and its known closest phylogenetic neighbors. These probes detect unique rRNA and gene sequences encoding rRNA, and may be used in an assay for the detection and/or quantitation of *Chlamydia pneumoniae*.

*Chlamydia pneumoniae* has been identified as a cause of both upper and lower respiratory tract infections. It has been shown to produce pneumonia in neonates and infants as well as in adults. It can also cause bronchitis, pharyngitis, and sinusitis and it may be a cause of chronic sinus infection in children. The disease has a gradual onset and often involves a sore throat, cough and hoarseness. These symptoms are similar to those of other atypical pneumonia, and thus clinical diagnosis is difficult.

*C. pneumoniae* is an obligatory intracellular organism. Two types of intracellular inclusions have been observed. An elementary body which is usually pear-shaped, but may be pleomorphic, and a reticulate body. Both genus specific and specific antigens are present on the elementary bodies. Laboratory diagnosis of *C. pneumoniae* is difficult. Definitive identification requires growth in HELA 299 cells or in yolk sac and multiple passages are often necessary. A flourescein-labeled species specific monoclonal antibody is then used to stain the inclusion bodies. Diagnosis by serological techniques generally requires two serum specimens, one of which is taken weeks to months after the initial specimen. Two specimens are necessary because of the large number of people (40–50%) who have antibodies to *C. pneumonia*. Confirmation of a current infection requires the demonstration of a rise in the IgG titer.

The use of a direct DNA-probe test of this invention for *C. pneumoniae* rRNA allows the conclusive identification of the presence of the organism in a clinical sample within 2 hours of sample collection.

Thus, in a first aspect, the invention features hybridization assay probes able to distinguish *Chlamydia pneumoniae* from other Chlamydia species.

In preferred embodiments, the probe is complementary to rRNA or rDNA, e.g., a variable region of rRNA; at least 50% of the nucleotides in the oligonucleotide probe are able to hybridize to a contiguous series of bases in at least one variable region of ribosomal nucleic acid in *Chlamydia pneumoniae*; the probe is a nucleotide polymer able to hybridize to the rRNA of the species *Chlamydia pneumoniae* in the region corresponding to bases 175–188, 224–247, 623–647 or 1008–1030 of *Escherichia coli* 16S rRNA or 1711–1733 of *Escherichia coli* 23S rRNA or a nucleotide polymer complementary thereto; and the oligonucleotide comprises, consists essentially of, or consists of at least a portion of at least 10 contiguous bases of the sequence (SEQ ID NO: 2) GCCTAATTACACTACATTCGG or (SEQ ID NO: 4) CTGATATCGCATAAACTCTTCCTC or (SEQ ID NO: 7) GATAGTTTTAAATGCTGACTTGGGG or (SEQ ID NO: 11) GCGGAAAGCTGTATTT-CTACAG or
(SEQ ID NO: 14) CGCTGGGTAATCACCTTAAG or oligonucleotides
complementary or homologous (e.g., the RNA encoded thereby) thereto, with or without a helper probe, as described below.

By "consists essentially of" is meant that the probe is provided as a purified nucleic acid which hybridizes under stringent hybridizing conditions with the desired organism and not with other related organisms. Such a probe may be linked to other nucleic acids which do not affect such hybridization. Generally, it is preferred that the probe be of between 15 and 100 (most preferably between 20 and 50) bases in size. It may, however, be provided in a vector.

In related aspects, the invention features a nucleotide polymer able to hybridize to the above oligonucleotides, a nucleic acid hybrid formed with the above oligonucleotides (useful for allowing detection of the presence of a specific oligonucleotide sequence), and a nucleic acid sequence substantially complementary thereto.

The probes of this invention offer a rapid, non-subjective method of identification and quantitation of a bacterial colony or sample of biologically relevant tissue for the presence of specific rRNA sequences unique to all strains of Chlamydia pneumoniae.

Other features and advantages of the invention will be apparent from the following description of the preferred embodiments thereof, and from the claims.

DESCRIPTION OF THE PREFERRED EMBODIMENTS PROBES

We have discovered DNA probes complementary to a particular rRNA sequence obtained from *Chlamydia pneumoniae*. Furthermore, we have successfully used those probes in a specific assay for the detection of *Chlamydia pneumoniae*, distinguishing *C. pneumoniae* from its known and presumably most closely related taxonomic or phylogenetic neighbors.

With the exception of viruses, all prokaryotic organisms contain rRNA genes encoding 5S rRNA, 16S rRNA and a larger rRNA molecule known as 23S rRNA. Using methods known to those skilled in the art, variable regions of rRNA sequences from the 16S rRNA of *Chlamydia pneumoniae* were identified as described below. Other such sequences can be identified using equivalent techniques. These methods include partially or fully sequencing the rRNA of *Chlamydia pneumoniae* and closely related phylogenetic neighbors, aligning the sequences to reveal areas of maximum homology, and examining the alignment for regions with sequence variation. The examples provided below are thus not limiting in this invention, With respect to sequencing, complementary oligonucleotide primers of about 10-100 bases in length were hybridized to conserved regions in purified rRNA that are specific to the 5S, 16S, or 23S subunits and extended with the enzyme reverse transcriptase. Chemical degradation or dideoxynucleotide-terminated sequencing reactions were used to determine the nucleotide sequence of the extended product. Lane et al., 82 *Proc. Natl Acad, Sci. USA*, 6955, 1985. In a less preferred method, genomic ribosomal RNA sequences may also be determined by standard procedure.

It is not always necessary to determine the entire nucleic acid sequence in order to obtain a probe sequence. Extension from any single oligonucleotide primer can yield up to 300-400 bases of sequence. When a single primer is used to partially sequence the rRNA of the target organism and organisms closely related to the target, an alignment can be made as outlined below. If a useful probe sequence is found, it is not necessary to continue rRNA sequencing using other primers. If, on the other hand, no useful probe sequence is obtained from sequencing with a first primer, or if higher sensitivity is desired, other primers can be used to obtain more sequences. In those cases where patterns of variation for a molecule are not well understood, more sequence data may be required prior to probe design.

After sequencing, the sequences are aligned to maximize homology. The rRNA molecule has a close relationship of secondary structure to function. This imposes restrictions on evolutionary changes in the primary sequence so that the secondary structure is maintained. For example, if a base is changed on one side of a helix, a compensating change is made on the other side to preserve the complementarity (this is referred to as co-variance). This allows two very different sequences to be aligned based on the conserved primary sequence and also on the conserved secondary structure elements. Once sequences are aligned it is possible to find the regions in which the primary sequence is variable.

We have identified variable regions by comparative analysis of rRNA sequences both published in the literature and sequences which we have determined. Computers and computer programs which may be used or adapted for the purposes herein disclosed are commercially available. Since the sequence evolution at each of the variable regions (for example, spanning a minimum of 10 nucleotides) is, for the most part, divergent, not convergent, we can confidently design probes based on a few rRNA sequences which differ between the target organism and its phylogenetically closest relatives. We have seen sufficient variation between the target organism and the closest phylogenetic relative found in the same sample to design the probe of interest.

We have identified the following useful guidelines for designing probes with desired characteristics. Because the extent and specificity of hybridization reactions such as those described herein are affected by a number of factors, manipulation of one or more of those factors will determine the exact sensitivity and specificity of a particular probe, whether perfectly complementary to its target or not. The importance and effect of various assay conditions, explained further herein, are known to those skilled in the art.

First, the stability of the probe:target nucleic acid hybrid should be chosen to be compatible with the assay conditions. This may be accomplished by avoiding long A and T rich sequences, by terminating the hybrids with G:C base pairs, and by designing the probe with an appropriate Tm. The beginning and end points of the probe should be chosen so that the length and % G and % C result in a Tm about 2°-10° C. higher than the temperature at which the final assay will be performed. The base composition of the probe is significant because G-C base pairs exhibit greater thermal stability as compared to A-T base pairs due to additional hydrogen bonding. Thus, hybridization involving complementary nucleic acids of higher G-C content will be stable at higher temperatures.

Conditions such as ionic strength and incubation temperature under which a probe will be used should also be taken into account in constructing a probe. It is known that hybridization will increase as the ionic strength of the reaction mixture increases, and that the thermal stability of hybrids will increase with increasing ionic strength. On the other hand, chemical reagents, such as formamide, urea, dimethylsulfoxide and alcohols, which disrupt hydrogen bonds, will increase the stringency of hybridization. Destabilization of the hydrogen bonds by such reagents can greatly reduce the Tm. In general, optimal hybridization for synthetic oligonucleotide probes of about 10-50 bases in length occurs approximately 5° C. below the melting temperature for a given duplex. Incubation at temperatures below the optimum may allow mismatched base sequences to hybridize and can therefore result in reduced specificity.

It is desirable to have probes which hybridize only under conditions of high stringency. Under high stringency conditions only highly complementary nucleic acid hybrids will form (i.e., those having at least about 14 out of 17 bases in a contiguous series of bases being complementary); hybrids without a sufficient degree of complementarity will not form. Accordingly, the stringency of the assay conditions determines the amount of complementarity needed between two nucleic acid strands forming a hybrid. Stringency is chosen to maximize the difference in stability between the hybrid formed with the target and the nontarget nucleic acid.

Second, probes should be positioned so as to minimize the stability of the probe:nontarget nucleic acid hybrid. This may be accomplished by minimizing the length of perfect complementarity to non-target organisms, avoiding G and C rich regions of homology to non-target sequences, and by positioning the probe to span as many destabilizing mismatches as possible. Whether a probe sequence is useful to detect only a specific type of organism depends largely on the thermal stability difference between probe:target hybrids and probe:nontarget hybrids. In designing probes, the differences in these Tm values should be as large as possible (e.g., at least 2° C. and preferably 5° C.).

The length of the target nucleic acid sequence and, accordingly, the length of the probe sequence can also be important. In some cases, there may be several sequences from a particular region, varying in location and length, which will yield probes with the desired hybridization characteristics. In other cases, one sequence may be significantly better than another which differs merely by a single base. While it is possible for nucleic acids that are not perfectly complementary to hybridize, the longest stretch of perfectly homologous base sequence will normally primarily determine hybrid stability. While oligonucleotide probes of different lengths and base composition may be used, oligonucleotide probes preferred in this invention are between about 10 to 50 bases in length and are sufficiently homologous to the target nucleic acid.

Third, regions of the rRNA which are known to form strong internal structures inhibitory to hybridization are less preferred. Likewise, probes with extensive self-complementarity should be avoided.

As explained above, hybridization is the association of two single strands of complementary nucleic acid to form a hydrogen bonded double strand. It is implicit that if one of the two strands is wholly or partially involved in a hybrid that it will be less able to participate in formation of a new hybrid. In the case of rRNA, the molecule is known to form very stable intramolecular hybrids. By designing a probe so that a substantial portion of the sequence of interest is single stranded, the rate and extent of hybridization may be greatly increased. If the target is the genomic sequence corresponding to the rRNA then it will naturally occur in a double stranded form, this is also the case with the product of the polymerase chain reaction (PCR). These double stranded targets are naturally inhibitory to hybridization with a probe. Finally, there can be intramolecular and intermolecular hybrids formed within a probe if there is sufficient self complementarity. Such structures can be avoided through careful probe design. Computer programs are available to search for this type of interaction.

Once a presumptive unique sequence has been identified, a complementary DNA oligonucleotide is produced. This single stranded oligonucleotide will serve as the probe in the hybridization reaction. Defined oligonucleotides may be produced by any of several well known methods, including automated solid-phase chemical synthesis using cyanoethylphosphoramidite precursors. Barone et al., 12 *Nucleic Acids Research* 4051, 1984. Other well-known methods for construction of synthetic oligonucleotides may, of course, be employed. 2 J. Sambrook, E. F. Fritsch and T. Maniatis, *Molecular Cloning* 11 (2d ed. 1989).

Once synthesized, selected oligonucleotide probes may also be labelled by any of several well known methods. 2 J. Sambrook, E. F. Fritsch and T. Maniatis, *Molecular Cloning* 11 (2d ed. 1989). Useful labels include radioisotopes as well as non-radioactive reporting groups. Isotopic labels include $^3$H, $^{35}$S, $^{32}$P, $^{125}$I, $^{57}$Cobalt and $^{14}$C. Most methods of isotopic labelling involve the use of enzymes and include the known methods of nick translation, end labelling, second strand synthesis, and reverse transcription. When using radio-labelled probes, hybridization can be detected by autoradiography, scintillation counting, or gamma counting. The detection method selected will depend upon the hybridization conditions and the particular radioisotope used for labelling.

Non-isotopic materials can also be used for labelling, and may be introduced internally into the sequence or at the end of the sequence. Modified nucleotides may be incorporated enzymatically or chemically and chemical modifications of the probe may be performed during or after synthesis of the probe, for example, by the use of non-nucleotide linker groups. Non-isotopic labels include fluorescent molecules, chemiluminescent molecules, enzymes, cofactors, enzyme substrates, haptens or other ligands. We currently prefer to use acridinium esters.

Following synthesis and purification of a particular oligonucleotide sequence, several procedures may be utilized to determine the acceptability of the final product. The first is polyacrylamide gel electrophoresis, which is used to determine size. 2 J. Sambrook, E. F. Fritsch and T. Maniatis, *Molecular Cloning*, 11.51 (2d ed. 1989). Such procedures are known in the art. In addition to polyacrylamide gel electrophoresis, High Performance Liquid Chromatography ("HPLC") procedures also may be used to determine the size and purity of the oligonucleotide product. These procedures are also known to those skilled in the art.

It will be appreciated by those skilled in the art that factors which affect the thermal stability can affect probe specificity and therefore, must be controlled. Thus, the melting profile, including the melting temperature (Tm) of the oligonucleotide/target hybrids should be determined. The preferred method is described in Arnold et al., patent application Ser. No. 613,603 filed Nov. 8, 1990, U.S. Pat. No. 5,283,174 entitled "Homogeneous Protection Assay", assigned to Gen-Probe Incorporated, Mar. 6, 1992, Reel/Frame 6057/0433-34 hereby incorporated by reference herein.

For Tm measurement using a Hybridization Protection Assay (HPA) the following technique is used. A probe:target hybrid is formed in target excess in a lithium succinate buffered solution containing lithium lauryl sulfate. Aliquots of this hybrid are diluted in the hybridization buffer and incubated for five minutes at various temperatures starting below that of the anticipated Tm (typically 55° C.) and increasing in 2-5 degree increments. This solution is then diluted with a mildly alkaline borate buffer and incubated at a lower temperature (for example 50° C.) for ten minutes. Under these conditions the acridinium ester attached to a single stranded probe is hydrolyzed while that attached to hybridized probe is relatively protected from hydrolysis. The amount of chemiluminescence remaining is proportional to the amount of hybrid, and is measured in a luminometer by addition of hydrogen peroxide followed by alkali. The data is plotted as percent of maximum signal (usually from the lowest temperature) versus temperature. The Tm is defined as the temperature at which 50% of the maximum signal remains.

In addition to the above method, oligonucleotide/target hybrid melting temperature may also be determined by isotopic methods well known to those skilled in the art. It should be noted that the Tm for a given hybrid will vary depending on the hybridization solution being used because the thermal stability depends upon the concentration of different salts, detergents, and other solutes which effect relative hybrid stability during thermal denaturation. 2 J. Sambrook, E. F. Fritsch and T. Maniatis, *Molecular Cloning*, 9.51 (2d ed. 1989).

Rate of hybridization may be measured by determining the $C_0t_{\frac{1}{2}}$. The rate at which a probe hybridizes to its target is a measure of the thermal stability of the target secondary structure in the probe region. The standard measurement of hybridization rate is the $C_0t_{\frac{1}{2}}$ which is measured as moles of nucleotide per liter times seconds. Thus, it is the concentration of probe times the time at which 50% of the maximal hybridization occurs at that concentration. This value is determined by hybridizing various amounts of probe to a constant amount of target for a fixed time. For example, 0.05 pmol of target is incubated with 0.012, 0.025, 0.05, 0.1 and 0.2 pmol of probe for 30 minutes. The amount of hybrid after 30 minutes is measured by HPA as described above. The signal is then plotted as a log of the percent of maximum Relative Light Units (RLU) (from the highest probe concentration) versus probe concentration (moles of nucleotide per liter). RLU are a measurement of the quantity of photons emitted by the labelled-probe measured by the luminometer. The $C_0t_{\frac{1}{2}}$ is found graphically from the concentration corresponding to 50% of maximum hybridization multiplied by the hybridization time in seconds. These values range from $9.0 \times 10^{-6}$ to $9 \times 10^{-5}$ with the preferred values being less than $3.5 \times 10^{-5}$.

As described by Kohne and Kacian (U.S. Ser. No. 816,711, entitled "Accelerated Nucleic Acid Reassociation Method," filed Jan. 7, 1986 abandoned in favor of U.S. application Ser. No. 644,879, filed Jan. 23, 1991 U.S. Pat. No. 5,132,207 allowed Feb. 7, 1992, assigned to Gen-Probe Incorporated Apr. 14, 1986, Reel/Frame 4538/0494 hereby incorporated by reference herein) other methods of nucleic acid reassociation can be used.

The following example sets forth synthetic probes complementary to a unique rRNA sequence, or the corresponding gene, from a target organism, *Chlamydia pneumoniae*, and their use in a hybridization assay.

EXAMPLE

Probes specific for *C. pneumoniae* were identified by sequencing with primers complementary to the 16S and 23S rRNA. The above listed sequences were characterized and shown to be specific for *Chlamydia pneumoniae*. The phylogenetically near neighbors *C. trachomatis* and *C. psittaci* were used as comparisons with the sequence of *C. pneumoniae*.

To demonstrate the reactivity and specificity of the probes for *C. pneumoniae*, they were used in a hybridization assay. The probes were first synthesized with a non-nucleotide linker, then labelled with a chemiluminescent acridinium ester as described in EPO Patent Application No. PCT/US88/03361, entitled "Acridinium Ester Labeling and Purification of Nucleotide Probes filed Oct. 5, 1988. The acridinium ester attached to unhybridized probe is rendered non-chemiluminescent under mild alkaline conditions, while the acridinium ester attached to hybridized probe is relatively resistant. Thus, it is possible to assay for hybridization of acridinium ester-labelled probe by incubation with an alkaline buffer, followed by detection of chemiluminescence in a luminometer. Results are given in RLU, the quantity of photons emitted by the labelled probe measured by the luminometer.

Nucleic acid hybridization was enhanced by the use of "Helper Probes" as disclosed in Hogan et al., U.S. Pat. No. 5,030,557 entitled "Means and Methods for Enhancing Nucleic Acid Hybridization", issued Jul. 9, 1991 and hereby incorporated by reference herein. RNA was hybridized to the acridinium ester-labeled probes in the presence of one or more unlabeled Helper Probes having oligonucleotide sequences as follows (written 5'-3'):

(SEQ ID NO: 1) TATTAGCGATCGTTTCCAACCGTTATCCCCAAGT,
(SEQ ID NO: 3) AACCGAAAGGTCGAAGATCCCCTTCTTTAATATATATTAGAT,
(SEQ ID NO: 5) GGGCTTTTACCCCACCAACAAG,
(SEQ ID NO: 6) TTGAGCCCCAAAATTTAACATCTAACTTTCCTTTCCGCC,
(SEQ ID NO: 8) CCCTTTTCCCCATCTATCCTCTAGAAA,
(SEQ ID NO: 9) CCACATGCTCCACTGCTTGTGCGGGCCCCCGTC,
(SEQ ID NO: 10) TTGTCAAATACATGTCAAGTCCAGGTAAGGTCCTTCGCG,
(SEQ ID NO: 12) GCTGACGACAGCCATGCAGCACCTGTGTATCTGTCCTT,
(SEQ ID NO: 13) AGGCTCCCCTTATTCGAAGTTACG, and
(SEQ ID NO: 15) CTCTGCGGCCCCCCAAGGCTCATAC.

In the following experiment, RNA released from $>10^7$ organisms was assayed. An example of such a method is provided by Murphy et al., U.S. Ser. No. 841,860, entitled "Method for Releasing RNA and DNA from Cells", filed Mar. 20, 1986, abandoned in favor of U.S. Ser. No. 298,765, filed Jan. 17, 1989, abandoned in favor of U.S. Ser. No. 711,114, filed Jun. 21, 1991, assigned to Gen-Probe Incorporated, May 23, 1986, Reel/Frame 4566/0901, hereby incorporated by reference herein. Following hybridization at 60° C. for one hour in 0.19M lithium succinate pH 5, 0.62M lithium lauryl sulfate, 3 mM ethylenediaminetetraacetic acid, 3 mM ethylene glycol bis (beta-amino ethyl ether) N,N,N',N' tetraacetic acid, hybrids were bound to magnetic particles in a solution containing 0.76M sodium borate pH 7.5 and washed once in a solution containing 80 mM sodium borate pH 10.4. The chemiluminescence associated with the particles is measured in a luminometer. RLU from a hybridization reaction containing 1 ng of non-target RNA was subtracted from the values shown. A net RLU value greater than +300 RLU was a positive reaction; less than +300 was a negative reaction.

The following data show that the five probes described above, and tested as a mix did not cross react with organisms from a wide phylogenetic cross section. Of course, each probe can be used alone in a hybridization assay.

| Organism | ATCC NO. | Net RLU[1] |
|---|---|---|
| Acinetobacter calcoaceticus | 33604 | −13 |
| Acinetobacter lwoffii | 15309 | −3 |
| Actinomyces israelii | 10049 | 14 |
| Actinomyces pyogenes | 19411 | 2 |
| Aerococcus viridans | 11563 | 32 |
| Aeromonas hydrophila | 7966 | 1 |
| Alcaligenes denitrificans | 27061 | 19 |
| Alcaligenes faecalis | 8750 | −7 |
| Bacillus subtilis | 6051 | 0 |
| Bacteroides fragilis | 23745 | −15 |
| Bordetella bronchiseptica | 10580 | 0 |
| Branhamella catarrhalis | 25238 | −10 |
| Brevibacterium linens | 9172 | −4 |
| Candida albicans | 18804 | 4 |
| Capnocytophaga ochracea | 27872 | −115 |
| Chlamydia pneumoniae[2] | 1310 | 436 |
| Chlamydia psittaci[2] | VR-656 | 2 |
| Chlamydia trachomatis[2] | VR-878 | 21 |
| Clostridium innocuum | 14501 | 9 |
| Clostridium pasteurianum | 6013 | −3 |
| Clostridium perfringens | 13124 | 2 |
| Clostridium ramosum | 25582 | −7 |
| Corynebacterium diphtheriae | 11913 | −9 |
| Corynebacterium haemolyticum | 9345 | −10 |
| C. pseudodiphtheriticum | 10700 | 1 |
| C. pseudotuberculosis | 19410 | −5 |
| Corynebacterium xerosis | 373 | −4 |
| Cryptococcus neoformans | 32045 | −2 |
| Deinococcus radiodurans | 35073 | −8 |
| Dermatophilus congolensis | 14637 | −3 |
| Derxia gummosa | 15994 | 148 |
| Enterococcus faecalis | 19433 | −12 |
| Erysipelothrix rhusiopathiae | 19414 | −2 |
| Escherichia coli | 10798 | −13 |
| Flavobacterium meningosepticum | 13253 | −22 |
| Gemella haemolysans | 10379 | −24 |
| Haemophilus influenzae | 19418 | −2 |
| Klebsiella pneumoniae | 23357 | −2 |
| Lactobacillus acidophilus | 4356 | −9 |
| Lactococcus lactis cremoris | 19257 | −7 |
| Legionella pneumophila | 33152 | −10 |
| Leuconostoc paramesenteroides | 33313 | −8 |
| Listeria monocytogenes | 35152 | −13 |
| Micrococcus kristinae | 27570 | −3 |
| Micrococcus luteus | 4698 | −7 |
| Moraxella osloensis | 19976 | −10 |
| Neisseria lactamica | 23970 | −1 |
| Neisseria meningitidis | 13077 | −7 |
| Neisseria mucosa | 19696 | −20 |
| Neisseria sicca | 29193 | −8 |
| Nocardia asteroides | 19247 | −1 |
| Oerskovia turbata | 33225 | −10 |
| Oerskovia xanthineolytica | 27402 | −7 |
| Paracoccus denitrificans | 17741 | −15 |
| Pediococcus acidilactici | 33314 | −9 |
| Peptostreptococcus magnus | 14955 | 4 |
| Peptostreptococcus anaerobius | 27337 | 120 |
| Propionibacterium acnes | 6919 | −31 |
| Proteus mirabilis | 25933 | −3 |
| Pseudomonas aeruginosa | 25330 | −14 |
| Rhodococcus bronchialis | 25592 | −15 |
| Rhodospirillum rubrum | 11170 | −7 |
| Staphylococcus aureus | 25923 | −8 |
| Staphylococcus aureus | 12598 | −15 |
| Staphylococcus aureus | 33591 | −3 |
| Staphylococcus epidermidis | 12228 | −11 |
| Streptococcus agalactiae | 13813 | −14 |
| Streptococcus mitis | 9811 | −10 |
| Streptococcus pneumoniae | 6303 | −6 |
| Streptococcus pyogenes | 19615 | −4 |
| Streptococcus sanguis | 10556 | −12 |
| Streptomyces griseus | 23345 | −15 |
| Vibrio parahaemolyticus | 17802 | −10 |
| Yersinia enterocolitica | 9610 | −15 |

[1]Experimental value - the value obtained with 1 ng of non-target rRNA.
[2]10 ng of extracted rRNA were assayed.

The above data show that the novel probes herein disclosed and claimed are capable of distinguishing *Chlamydia pneumoniae* from its known nearest phylogenetic neighbors.

Other embodiments are within the following claims.

We claim:

1. A nucleotide polymer having the sequence (SEQ ID NO: 2) 5' GCCTAATTACACTACATTCGG 3' or the complement thereof, (SEQ ID NO: 16) 5'CCGAATGTAGTGTAATTAGGC 3', wherein said nucleotide polymer hybridizes under stringent hybridization conditions to nucleic acid of *Chlamydia pneumoniae,* and not to nucleic acid of *Chlamydia psittaci* or *Chlamydia trachomatis.*

2. A nucleotide polymer having the sequence (SEQ ID NO: 4) 5' CTGATATCGCATAAACTCTTCCTC 3' or the complement thereof, (SEQ ID NO: 17) 5' GAGGAAGAGTTTATGCGATATCAG 3' wherein said nucleotide polymer hybridizes under stringent hybridization conditions to nucleic acid of *Chlamydia pneumoniae,* and not to nucleic acid of *Chlamydia psittaci* or *Chlamydia trachomatis.*

3. A nucleotide polymer having the sequence (SEQ ID NO: 7) 5'GATAGTTTTAAATGCTGACTTGGGG 3' or the complement thereof, (SEQ ID NO: 18) 5' CCCCAAGTCAGCATTTAAAACTATC 3' wherein said nucleotide polymer hybridizes under stringent hybridization conditions to nucleic acid of *Chlamydia pneumoniae,* and not to nucleic acid of *Chlamydia psittaci* or *Chlamydia trachomatis.*

4. A nucleotide polymer having the sequence (SEQ ID NO: 11) 5' GCGGAAAGCTGTATTTCTACAG 3' or the complement thereof, (SEQ ID NO: 19) 5' CTGTAGAAATACAGCTTTCCGC 3', wherein said nucleotide polymer hybridizes under stringent hybridization conditions to nucleic acid of *Chlamydia pneumoniae,* and not to nucleic acid of *Chlamydia psittaci* or *Chlamydia trachomatis.*

5. A nucleotide polymer having the sequence (SEQ ID NO: 14) 5' CGCTGGGTAA TCACCTTAAG 3', or the complement thereof, (SEQ ID NO: 20) 5' CTTAAGGTGATTACCCAGCG 3' wherein said nucleotide polymer hybridizes under stringent hybridization conditions to nucleic acid of *Chlamydia pneumoniae,* and not to nucleic acid of *Chlamydia psittaci* or *Chlamydia trachomatis.*

6. A nucleic acid hybrid formed between a nucleotide polymer of claim 1 and a nucleic acid sufficiently complementary thereto to form a hybrid therewith in 0.19M lithium succinate, 0.62M lithium lauryl sulfate at 60° C.

7. A nucleic acid hybrid formed between a nucleotide polymer of claim 2 and a nucleic acid sufficiently complementary thereto to form a hybrid therewith in 0.19M lithium succinate, 0.62M lithium lauryl sulfate at 60° C.

8. A nucleic acid hybrid formed between a nucleotide polymer of claim 3 and a nucleic acid sufficiently complementary thereto to form a hybrid therewith in 0.19M lithium succinate, 0.62M lithium lauryl sulfate at 60° C.

9. A nucleic acid hybrid formed between a nucleotide polymer of claim 4 and a nucleic acid sufficiently complementary thereto to form a hybrid therewith in 0.19M lithium succinate, 0.62M lithium lauryl sulfate at 60° C.

10. A nucleic acid hybrid formed between a nucleotide polymer of claim 5 and a nucleic acid sufficiently complementary thereto to form a hybrid therewith in 0.19M lithium succinate, 0.62M lithium lauryl sulfate at 60° C.

11. A probe mix comprising the polymer of claim 1 and a nucleic acid helper probe.

12. A probe mix comprising the polymer of claim 2 and a nucleic acid helper probe.

13. A probe mix comprising the polymer of claim 3 and a nucleic acid helper probe.

14. A probe mix comprising the polymer of claim 4 and a nucleic acid helper probe.

15. A probe mix comprising the polymer of claim 5 and a nucleic acid helper probe.

16. The probe mix of claim 11, wherein said helper probe is an oligonucleotide having the oligonucleotide sequence (SEQ ID NO: 1) 5' TATTAGCGATCGTTTCCAACCGTTATCCCCAAGT 3' and/or (SEQ ID NO: 3) 5' AACCGAAAGGTCGAAGATCCCCTTCTTTAATATATATTAGAT 3' or the complements thereof, (SEQ ID NO: 31) 5' ACTTGGGGATAACGGTTGGAAACGATCGCTAATA 3', and (SEQ ID NO: 32) 5'ATCTAATATATTAAAGAAGGGGATCTTCGGACCTTTCGGTT 3'.

17. The probe mix of claim 12, wherein said helper probe is an oligonucleotide having the oligonucleotide sequence (SEQ ID NO: 3) 5' AACCGAAAGGTCGAAGATCCCCTTCTTTAATATATATTAGAT 3' and/or (SEQ ID NO:5) 5' GGGCTTTTACCCCACCAACAAG 3' or the complements thereof, (SEQ ID NO: 32) 5' ATCTAATATATTAAAGAAGGGGATCTTCGGACCTTTCGGTT 3', and (SEQ ID NO: 33) 5' CTTGTTGGTGGGGTAAAAGCCC 3'.

18. The probe mix of claim 13, wherein said helper probe is an oligonucleotide having the oligonucleotide sequence (SEQ ID NO: 6) 5' TTGAGCCCCAAAATTTAACATCTAACTTTCCTTTCCGCC 3' and/or (SEQ ID NO: 8) 5' CCCTTTTCCCCATCTATCCTCTAGAAA 3' or the complements thereof, (SEQ ID NO: 34) 5' GGCGGAAAGGAAAGTTAGATGTTAAATTTTGGGGCTCAA 3', and (SEQ ID NO: 35) 5' TTTCTAGAGGATAGATGGGGAAAAGGG 3'.

19. The probe mix of claim 14, wherein said helper probe is an oligonucleotide having the oligonucleotide sequence (SEQ ID NO: 9) 5' CCACATGCTCCACTGCTTGTGCGGGCCCCCGTC 3' and/or (SEQ ID NO: 10) 5' TTGTCAAATACATGTCAAGTCCAGGTAAGGTCCTTCGCG 3' and/or (SEQ ID NO: 12) 5′GCTGACGACAGCCATGCAGCACCTGTGTATCTGTCCTT 3′ or the complements thereof, (SEQ ID NO: 36) 5′GACGGGGGCCCGCACAAGCAGTGGAGCATGTGG 3′, (SEQ ID NO: 37) 5′CGCGAAGGACCTTACCTGGACTTGACATGTATTTGACAA 3′, and (SEQ ID NO: 38) 5′AAGGACAGATACACAGGTGCTGCATGGCTGTCGTCAGC 3′.

20. The probe mix of claim 15, wherein said helper probe is an oligonucleotide having the oligonucleotide sequence (SEQ ID NO: 13) 5′ AGGCTCCCCTTATTCCGAAGTTACG 3′ and/or (SEQ ID NO: 15) 5′ CTCTGCGGCCCCCCAAGGCTCATAC 3′ or the complements thereof, (SEQ ID NO: 39) 5′CGTAACTTCGGAATAAGGGGAGCCT 3′, and (SEQ ID NO: 40) 5′ GTATGAGCCTTGGGGGGCCGCAGAG 3′.

* * * * *

UNITED STATES PATENT AND TRADEMARK OFFICE
CERTIFICATE OF CORRECTION

PATENT NO. : 5,374,718
DATED : December 20, 1994
INVENTOR(S) : Hammond, Philip et al.

It is certified that error appears in the above-indentified patent and that said Letters Patent is hereby corrected as shown below:

Column 23, last line in each claim

Claim 1 : please delete "[or Chlamydia trachomatis]"

Claim 2: please delete "[or Chlamydia trachomatis]"

Claim 3: please delete "[or Chlamydia trachomatis]"

Claim 4: please delete "[or Chlamydia trachomatis]"

Claim 5: please delete "[or Chlamydia trachomatis]"

Signed and Sealed this

Twenty-seventh Day of June, 1995

Attest:

BRUCE LEHMAN

*Attesting Officer*     *Commissioner of Patents and Trademarks*

SEQUENCE LISTING ( 1 ) GENERAL INFORMATION:

( i i i ) NUMBER OF SEQUENCES: 40

( 2 ) INFORMATION FOR SEQ ID NO: 1:

( i ) SEQUENCE CHARACTERISTICS:
        ( A ) LENGTH: 34
        ( B ) TYPE: nucleic acid
        ( C ) STRANDEDNESS: single
        ( D ) TOPOLOGY: linear ( i i ) SEQUENCE DESCRIPTION: SEQ ID NO: 1:

TATTAGCGAT CGTTTCCAAC CGTTATCCCC AAGT    3 4

( 2 ) INFORMATION FOR SEQ ID NO: 2:

( i ) SEQUENCE CHARACTERISTICS:
    ( A ) LENGTH: 21
    ( B ) TYPE: nucleic acid
    ( C ) STRANDEDNESS: single
    ( D ) TOPOLOGY: linear ( i i ) SEQUENCE DESCRIPTION: SEQ ID NO: 2:

GCCTAATTAC ACTACATTCG G                               21

( 2 ) INFORMATION FOR SEQ ID NO: 3:

( i ) SEQUENCE CHARACTERISTICS:
        ( A ) LENGTH: 43
        ( B ) TYPE: nucleic acid
        ( C ) STRANDEDNESS: single
        ( D ) TOPOLOGY: linear ( i i ) SEQUENCE DESCRIPTION: SEQ ID NO: 3:

AACCGAAAGG TCCGAAGATC CCCTTCTTTA ATATATATTA GAT       43

( 2 ) INFORMATION FOR SEQ ID NO: 4:

( i ) SEQUENCE CHARACTERISTICS:
        ( A ) LENGTH: 24
        ( B ) TYPE: nucleic acid
        ( C ) STRANDEDNESS: single
        ( D ) TOPOLOGY: linear ( i i ) SEQUENCE DESCRIPTION: SEQ ID NO: 4:

CTGATATCGC ATAAACTCTT CCTC                            24

( 2 ) INFORMATION FOR SEQ ID NO: 5:

( i ) SEQUENCE CHARACTERISTICS:
        ( A ) LENGTH: 22
        ( B ) TYPE: nucleic acid
        ( C ) STRANDEDNESS: single
        ( D ) TOPOLOGY: linear ( i i ) SEQUENCE DESCRIPTION: SEQ ID NO: 5:

GGGCTTTTAC CCCACCAACA AG                              22

( 2 ) INFORMATION FOR SEQ ID NO: 6:

( i ) SEQUENCE CHARACTERISTICS:
        ( A ) LENGTH: 39
        ( B ) TYPE: nucleic acid
        ( C ) STRANDEDNESS: single
        ( D ) TOPOLOGY: linear ( i i ) SEQUENCE DESCRIPTION: SEQ ID NO: 6:

TTGAGCCCCA AAATTTAACA TCTAACTTTC CTTTCCGCC            39

( 2 ) INFORMATION FOR SEQ ID NO: 7:

( i ) SEQUENCE CHARACTERISTICS:
        ( A ) LENGTH: 25
        ( B ) TYPE: nucleic acid
        ( C ) STRANDEDNESS: single
        ( D ) TOPOLOGY: linear ( i i ) SEQUENCE DESCRIPTION: SEQ ID NO: 7:

GATAGTTTTA AATGCTGACT TGGGG                           25

( 2 ) INFORMATION FOR SEQ ID NO: 8:

( i ) SEQUENCE CHARACTERISTICS:
        ( A ) LENGTH: 27
        ( B ) TYPE: nucleic acid
        ( C ) STRANDEDNESS: single ( D ) TOPOLOGY: linear ( i i ) SEQUENCE DESCRIPTION: SEQ ID NO: 8:

CCCTTTTCCC CATCTATCCT CTAGAAA                27

( 2 ) INFORMATION FOR SEQ ID NO: 9:

( i ) SEQUENCE CHARACTERISTICS:
        ( A ) LENGTH: 33
        ( B ) TYPE: nucleic acid
        ( C ) STRANDEDNESS: single
        ( D ) TOPOLOGY: linear ( i i ) SEQUENCE DESCRIPTION: SEQ ID NO: 9:

CCACATGCTC CACTGCTTGT GCGGGCCCCC GTC            33

( 2 ) INFORMATION FOR SEQ ID NO: 10:

( i ) SEQUENCE CHARACTERISTICS:
        ( A ) LENGTH: 39
        ( B ) TYPE: nucleic acid
        ( C ) STRANDEDNESS: single
        ( D ) TOPOLOGY: linear ( i i ) SEQUENCE DESCRIPTION: SEQ ID NO: 10:

TTGTCAAATA CATGTCAAGT CCAGGTAAGG TCCTTCGCG       39

( 2 ) INFORMATION FOR SEQ ID NO: 11:

( i ) SEQUENCE CHARACTERISTICS:
        ( A ) LENGTH: 22
        ( B ) TYPE: nucleic acid
        ( C ) STRANDEDNESS: single
        ( D ) TOPOLOGY: linear ( i i ) SEQUENCE DESCRIPTION: SEQ ID NO: 11:

GCGGAAAGCT GTATTTCTAC AG                      22

( 2 ) INFORMATION FOR SEQ ID NO: 12:

( i ) SEQUENCE CHARACTERISTICS:
        ( A ) LENGTH: 38
        ( B ) TYPE: nucleic acid
        ( C ) STRANDEDNESS: single
        ( D ) TOPOLOGY: linear ( i i ) SEQUENCE DESCRIPTION: SEQ ID NO: 12:

GCTGACGACA GCCATGCAGC ACCTGTGTAT CTGTCCTT       38

( 2 ) INFORMATION FOR SEQ ID NO: 13:

( i ) SEQUENCE CHARACTERISTICS:
        ( A ) LENGTH: 25
        ( B ) TYPE: nucleic acid
        ( C ) STRANDEDNESS: single
        ( D ) TOPOLOGY: linear ( i i ) SEQUENCE DESCRIPTION: SEQ ID NO: 13:

AGGCTCCCCT TATTCCGAAG TTACG                   25

( 2 ) INFORMATION FOR SEQ ID NO: 14:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i i ) SEQUENCE DESCRIPTION: SEQ ID NO: 14:

CGCTGGGTAA TCACCTTAAG                    20

( 2 ) INFORMATION FOR SEQ ID NO: 15:

( i ) SEQUENCE CHARACTERISTICS:
        ( A ) LENGTH: 25
        ( B ) TYPE: nucleic acid
        ( C ) STRANDEDNESS: single
        ( D ) TOPOLOGY: linear ( i i ) SEQUENCE DESCRIPTION: SEQ ID NO: 15:

CTCTGCGGCC CCCCAAGGCT CATAC                    25

( 2 ) INFORMATION FOR SEQ ID NO: 16:

( i ) SEQUENCE CHARACTERISTICS:
        ( A ) LENGTH: 21
        ( B ) TYPE: nucleic acid
        ( C ) STRANDEDNESS: single
        ( D ) TOPOLOGY: linear ( i i ) SEQUENCE DESCRIPTION: SEQ ID NO: 16:

CCGAATGTAG TGTAATTAGG C                    21

( 2 ) INFORMATION FOR SEQ ID NO: 17:

( i ) SEQUENCE CHARACTERISTICS:
        ( A ) LENGTH: 24
        ( B ) TYPE: nucleic acid
        ( C ) STRANDEDNESS: single
        ( D ) TOPOLOGY: linear ( i i ) SEQUENCE DESCRIPTION: SEQ ID NO: 17:

GAGGAAGAGT TTATGCGATA TCAG                    24

( 2 ) INFORMATION FOR SEQ ID NO: 18:

( i ) SEQUENCE CHARACTERISTICS:
        ( A ) LENGTH: 25
        ( B ) TYPE: nucleic acid
        ( C ) STRANDEDNESS: single
        ( D ) TOPOLOGY: linear ( i i ) SEQUENCE DESCRIPTION: SEQ ID NO: 18:

CCCCAAGTCA GCATTTAAAA CTATC                    25

( 2 ) INFORMATION FOR SEQ ID NO: 19:

( i ) SEQUENCE CHARACTERISTICS:
        ( A ) LENGTH: 22
        ( B ) TYPE: nucleic acid
        ( C ) STRANDEDNESS: single
        ( D ) TOPOLOGY: linear ( i i ) SEQUENCE DESCRIPTION: SEQ ID NO: 19:

CTGTAGAAAT ACAGCTTTCC GC                    22

( 2 ) INFORMATION FOR SEQ ID NO: 20:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i i ) SEQUENCE DESCRIPTION: SEQ ID NO: 20:

CTTAAGGTGA TTACCCAGCG                    20

( 2 ) INFORMATION FOR SEQ ID NO: 21:

( i ) SEQUENCE CHARACTERISTICS:
    ( A ) LENGTH: 21
    ( B ) TYPE: nucleic acid
    ( C ) STRANDEDNESS: single
    ( D ) TOPOLOGY: linear ( i i ) SEQUENCE DESCRIPTION: SEQ ID NO: 21:

GCCUAAUUAC ACUACAUUCG G    21

( 2 ) INFORMATION FOR SEQ ID NO: 22:

( i ) SEQUENCE CHARACTERISTICS:
        ( A ) LENGTH: 24
        ( B ) TYPE: nucleic acid
        ( C ) STRANDEDNESS: single
        ( D ) TOPOLOGY: linear ( i i ) SEQUENCE DESCRIPTION: SEQ ID NO: 22:

CUGAUAUCGC AUAAACUCUU CCUC    24

( 2 ) INFORMATION FOR SEQ ID NO: 23:

( i ) SEQUENCE CHARACTERISTICS:
        ( A ) LENGTH: 25
        ( B ) TYPE: nucleic acid
        ( C ) STRANDEDNESS: single
        ( D ) TOPOLOGY: linear ( i i ) SEQUENCE DESCRIPTION: SEQ ID NO: 23:

GAUAGUUUUA AAUGCUGACU UGGGG    25

( 2 ) INFORMATION FOR SEQ ID NO: 24:

( i ) SEQUENCE CHARACTERISTICS:
        ( A ) LENGTH: 22
        ( B ) TYPE: nucleic acid
        ( C ) STRANDEDNESS: single
        ( D ) TOPOLOGY: linear ( i i ) SEQUENCE DESCRIPTION: SEQ ID NO: 24:

GCGGAAAGCU GUAUUUCUAC AG    22

( 2 ) INFORMATION FOR SEQ ID NO: 25:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i i ) SEQUENCE DESCRIPTION: SEQ ID NO: 25:

CGCUGGGUAA UCACCUUAAG    20

( 2 ) INFORMATION FOR SEQ ID NO: 26:

( i ) SEQUENCE CHARACTERISTICS:
        ( A ) LENGTH: 21
        ( B ) TYPE: nucleic acid
        ( C ) STRANDEDNESS: single
        ( D ) TOPOLOGY: linear ( i i ) SEQUENCE DESCRIPTION: SEQ ID NO: 26:

CCGAAUGUAG UGUAAUUAGG C    21

( 2 ) INFORMATION FOR SEQ ID NO: 27:

( i ) SEQUENCE CHARACTERISTICS:
        ( A ) LENGTH: 24
        ( B ) TYPE: nucleic acid ( C ) STRANDEDNESS: single
( D ) TOPOLOGY: linear ( i i ) SEQUENCE DESCRIPTION: SEQ ID NO: 27:

GAGGAAGAGU UUAUGCGAUA UCAG   24

( 2 ) INFORMATION FOR SEQ ID NO: 28:

( i ) SEQUENCE CHARACTERISTICS:
( A ) LENGTH: 25
( B ) TYPE: nucleic acid
( C ) STRANDEDNESS: single
( D ) TOPOLOGY: linear ( i i ) SEQUENCE DESCRIPTION: SEQ ID NO: 28:

CCCCAAGUCA GCAUUUAAAA CUAUC   25

( 2 ) INFORMATION FOR SEQ ID NO: 29:

( i ) SEQUENCE CHARACTERISTICS:
( A ) LENGTH: 22
( B ) TYPE: nucleic acid
( C ) STRANDEDNESS: single
( D ) TOPOLOGY: linear ( i i ) SEQUENCE DESCRIPTION: SEQ ID NO: 29:

CUGUAGAAAU ACAGCUUUCC GC   22

( 2 ) INFORMATION FOR SEQ ID NO: 30:

( i ) SEQUENCE CHARACTERISTICS:
( A ) LENGTH: 20
( B ) TYPE: nucleic acid
( C ) STRANDEDNESS: single
( D ) TOPOLOGY: linear ( i i ) SEQUENCE DESCRIPTION: SEQ ID NO: 30:

CUUAAGGUGA UUACCCAGCG   20

( 2 ) INFORMATION FOR SEQ ID NO: 31:

( i ) SEQUENCE CHARACTERISTICS:
( A ) LENGTH: 34
( B ) TYPE: nucleic acid
( C ) STRANDEDNESS: single
( D ) TOPOLOGY: linear ( i i ) SEQUENCE DESCRIPTION: SEQ ID NO: 31:

ACTTGGGGAT AACGGTTGGA AACGATCGCT AATA   34

( 2 ) INFORMATION FOR SEQ ID NO: 32:

( i ) SEQUENCE CHARACTERISTICS:
( A ) LENGTH: 43
( B ) TYPE: nucleic acid
( C ) STRANDEDNESS: single
( D ) TOPOLOGY: linear ( i i ) SEQUENCE DESCRIPTION: SEQ ID NO: 32:

ATCTAATATA TATTAAAGAA GGGGATCTTC GGACCTTTCG GTT   43

( 2 ) INFORMATION FOR SEQ ID NO: 33:

( i ) SEQUENCE CHARACTERISTICS:
( A ) LENGTH: 22
( B ) TYPE: nucleic acid
( C ) STRANDEDNESS: single
( D ) TOPOLOGY: linear ( i i ) SEQUENCE DESCRIPTION: SEQ ID NO: 33:

CTTGTTGGTG GGGTAAAAGC CC 22

(2) INFORMATION FOR SEQ ID NO: 34:

(i) SEQUENCE CHARACTERISTICS:
        (A) LENGTH: 39
        (B) TYPE: nucleic acid
        (C) STRANDEDNESS: single
        (D) TOPOLOGY: linear (ii) SEQUENCE DESCRIPTION: SEQ ID NO: 34:

GGCGGAAAGG AAAGTTAGAT GTTAAATTTT GGGGCTCAA 39

(2) INFORMATION FOR SEQ ID NO: 35:

(i) SEQUENCE CHARACTERISTICS:
        (A) LENGTH: 27
        (B) TYPE: nucleic acid
        (C) STRANDEDNESS: single
        (D) TOPOLOGY: linear (ii) SEQUENCE DESCRIPTION: SEQ ID NO: 35:

TTTCTAGAGG ATAGATGGGG AAAAGGG 27

(2) INFORMATION FOR SEQ ID NO: 36:

(i) SEQUENCE CHARACTERISTICS:
        (A) LENGTH: 33
        (B) TYPE: nucleic acid
        (C) STRANDEDNESS: single
        (D) TOPOLOGY: linear (ii) SEQUENCE DESCRIPTION: SEQ ID NO: 36:

GACGGGGGCC CGCACAAGCA GTGGAGCATG TGG 33

(2) INFORMATION FOR SEQ ID NO: 37:

(i) SEQUENCE CHARACTERISTICS:
        (A) LENGTH: 39
        (B) TYPE: nucleic acid
        (C) STRANDEDNESS: single
        (D) TOPOLOGY: linear (ii) SEQUENCE DESCRIPTION: SEQ ID NO: 37:

CGCGAAGGAC CTTACCTGGA CTTGACATGT ATTTGACAA 39

(2) INFORMATION FOR SEQ ID NO: 38:

(i) SEQUENCE CHARACTERISTICS:
        (A) LENGTH: 38
        (B) TYPE: nucleic acid
        (C) STRANDEDNESS: single
        (D) TOPOLOGY: linear (ii) SEQUENCE DESCRIPTION: SEQ ID NO: 38:

AAGGACAGAT ACACAGGTGC TGCATGGCTG TCGTCAGC 38

(2) INFORMATION FOR SEQ ID NO: 39:

(i) SEQUENCE CHARACTERISTICS:
        (A) LENGTH: 25
        (B) TYPE: nucleic acid
        (C) STRANDEDNESS: single
        (D) TOPOLOGY: linear (ii) SEQUENCE DESCRIPTION: SEQ ID NO: 39:

CGTAACTTCG GAATAAGGGG AGCCT 25

( 2 ) INFORMATION FOR SEQ ID NO: 40:

( i ) SEQUENCE CHARACTERISTICS:
        ( A ) LENGTH: 25
        ( B ) TYPE: nucleic acid
        ( C ) STRANDEDNESS: single
        ( D ) TOPOLOGY: linear ( i i ) SEQUENCE DESCRIPTION: SEQ ID NO: 40:

GTATGAGCCT TGGGGGGCCG CAGAG        25